(12) United States Patent
Reeder et al.

(10) Patent No.: US 8,766,804 B2
(45) Date of Patent: *Jul. 1, 2014

(54) SYSTEM FOR MONITORING CAREGIVERS AND EQUIPMENT

(71) Applicant: Hill-Rom Services, Inc, Batesville, IN (US)

(72) Inventors: Ryan A. Reeder, Brookville, IN (US); Kenneth L. Kramer, Tai Po (HK); William L. Jacques, Mount Pleasant, SC (US); Carl W. Riley, Milan, IN (US); Richard J. Schuman, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/939,329

(22) Filed: Jul. 11, 2013

(65) Prior Publication Data

US 2013/0300558 A1    Nov. 14, 2013

Related U.S. Application Data

(63) Continuation of application No. 13/599,110, filed on Aug. 30, 2012, now Pat. No. 8,487,774, which is a continuation of application No. 13/238,899, filed on Sep. 21, 2011, now Pat. No. 8,258,965, which is a continuation of application No. 12/258,058, filed on Oct. 24, 2008, now Pat. No. 8,026,821, which is a continuation of application No. 11/075,979, filed on Mar. 9, 2005, now Pat. No. 7,443,302, which is a continuation of application No. 09/849,688, filed on May 4, 2001, now Pat. No. 6,876,303.

(60) Provisional application No. 60/202,283, filed on May 5, 2000, provisional application No. 60/202,284, filed on May 5, 2000, provisional application No. 60/229,136, filed on Aug. 30, 2000.

(51) Int. Cl.
*G08B 23/00* (2006.01)

(52) U.S. Cl.
USPC .............. 340/573.1; 340/539.12; 340/286.07; 340/825.49; 340/825.69; 128/903; 128/904; 600/300; 600/301

(58) Field of Classification Search
USPC ................. 340/573.1, 286.06, 286.07, 539.1, 340/539.12, 539.13, 825.49, 825.52, 340/825.69, 825.72; 128/903, 904; 600/300, 301

See application file for complete search history.

(56) References Cited

U.S. PATENT DOCUMENTS

| 4,850,040 A | 7/1989 | Teich et al. |
| 5,003,984 A | 4/1991 | Muraki et al. |
| 5,036,852 A | 8/1991 | Leishman |

(Continued)

OTHER PUBLICATIONS

"Cricket v2 User Manual," MIT Computer Science and Artificial Intelligence Lab, Jan. 2005.

(Continued)

*Primary Examiner* — Hung T. Nguyen
(74) *Attorney, Agent, or Firm* — Barnes & Thornburg LLP

(57) ABSTRACT

A hospital monitoring system for monitoring hospital personnel, a plurality of patient locations for patients, and associated devices is configured to control the associated devices based on the presence of hospital personnel or alarms.

18 Claims, 15 Drawing Sheets

(56) References Cited

U.S. PATENT DOCUMENTS

| | | | |
|---|---|---|---|
| 5,228,449 A | 7/1993 | Christ et al. | |
| 5,291,399 A | 3/1994 | Chaco et al. | |
| 5,319,363 A * | 6/1994 | Welch et al. ............ 340/8.1 |
| 5,394,882 A | 3/1995 | Mawhinney et al. | |
| 5,415,167 A | 5/1995 | Wilk et al. | |
| 5,417,222 A | 5/1995 | Dempsey et al. | |
| 5,511,553 A | 4/1996 | Segalowitz et al. | |
| 5,515,426 A | 5/1996 | Yacenda et al. | |
| 5,534,851 A | 7/1996 | Russek | |
| 5,537,095 A | 7/1996 | Dick et al. | |
| 5,544,661 A | 8/1996 | Davis et al. | |
| 5,561,412 A | 10/1996 | Novak et al. | |
| 5,579,775 A | 12/1996 | Dempsey et al. | |
| 5,594,786 A | 1/1997 | Chaco et al. | |
| 5,628,324 A | 5/1997 | Sarbach | |
| 5,633,627 A * | 5/1997 | Newham ............ 340/573.4 |
| 5,664,270 A | 9/1997 | Bell et al. | |
| 5,678,562 A | 10/1997 | Sellers et al. | |
| 5,687,771 A | 11/1997 | Clough et al. | |
| 5,689,229 A | 11/1997 | Chaco et al. | |
| 5,699,038 A | 12/1997 | Ulrich et al. | |
| 5,712,795 A | 1/1998 | Layman et al. | |
| 5,713,856 A | 2/1998 | Eggers et al. | |
| 5,719,761 A | 2/1998 | Gatti et al. | |
| 5,724,025 A | 3/1998 | Tavori | |
| 5,738,102 A | 4/1998 | Lemelson | |
| 5,772,599 A | 6/1998 | Nevo et al. | |
| 5,781,442 A | 7/1998 | Engleson et al. | |
| 5,800,387 A | 9/1998 | Duffy et al. | |
| 5,808,552 A | 9/1998 | Wiley et al. | |
| 5,822,418 A | 10/1998 | Yacenda et al. | |
| 5,822,544 A * | 10/1998 | Chaco et al. ............ 705/2 |
| 5,825,283 A | 10/1998 | Camhi et al. | |
| 5,836,910 A | 11/1998 | Duffy et al. | |
| 5,838,223 A | 11/1998 | Gallant et al. | |
| 5,862,803 A | 1/1999 | Besson et al. | |
| 5,867,821 A | 2/1999 | Ballantyne et al. | |
| 5,873,369 A | 2/1999 | Laniado et al. | |
| 5,919,141 A | 7/1999 | Money et al. | |
| 5,941,846 A | 8/1999 | Duffy et al. | |
| 5,944,659 A | 8/1999 | Flach et al. | |
| 5,957,854 A | 9/1999 | Besson et al. | |
| 5,990,866 A | 11/1999 | Yollin et al. | |
| 6,009,333 A | 12/1999 | Chaco et al. | |
| 6,014,346 A | 1/2000 | Malone et al. | |
| 6,028,519 A | 2/2000 | Dessureau et al. | |
| 6,038,469 A | 3/2000 | Karlsson et al. | |
| 6,044,283 A | 3/2000 | Fein et al. | |
| 6,044,382 A | 3/2000 | Martino et al. | |
| 6,047,203 A | 4/2000 | Sackner et al. | |
| 6,057,758 A | 5/2000 | Dempsey et al. | |
| 6,067,019 A | 5/2000 | Scott et al. | |
| 6,074,345 A | 6/2000 | Van Oostrom et al. | |
| 6,078,261 A | 6/2000 | Davsko et al. | |
| 6,080,106 A | 6/2000 | Lloyd et al. | |
| 6,093,146 A | 7/2000 | Filangeri et al. | |
| 6,125,350 A | 9/2000 | Dirbas et al. | |
| 6,132,371 A | 10/2000 | Dempsey et al. | |
| 6,135,949 A | 10/2000 | Russo et al. | |
| 6,147,592 A | 11/2000 | Ulrich et al. | |
| 6,147,618 A | 11/2000 | Halleck et al. | |
| 6,150,951 A | 11/2000 | Olejniczak | |
| 6,159,147 A | 12/2000 | Lichter et al. | |
| 6,160,478 A | 12/2000 | Jacobsen et al. | |
| 6,167,258 A | 12/2000 | Schmidt et al. | |
| 6,171,264 B1 | 1/2001 | Bader | |
| 6,186,962 B1 | 2/2001 | Lloyd et al. | |
| 6,198,394 B1 | 3/2001 | Jacobsen et al. | |
| 6,213,942 B1 | 4/2001 | Flach et al. | |
| 6,259,355 B1 * | 7/2001 | Chaco et al. ............ 340/286.07 |
| 6,270,457 B1 | 8/2001 | Bardy | |
| 6,277,080 B1 | 8/2001 | Nissilä et al. | |
| 6,289,238 B1 | 9/2001 | Besson et al. | |
| 6,304,774 B1 | 10/2001 | Gorman | |
| 6,336,900 B1 | 1/2002 | Alleckson et al. | |
| 6,336,903 B1 | 1/2002 | Bardy | |
| 6,368,284 B1 | 4/2002 | Bardy | |
| 6,398,727 B1 | 6/2002 | Bui et al. | |
| 6,398,728 B1 | 6/2002 | Bardy | |
| 6,402,691 B1 | 6/2002 | Peddicord et al. | |
| 6,406,426 B1 | 6/2002 | Reuss et al. | |
| 6,407,335 B1 | 6/2002 | Franklin-Lees et al. | |
| 6,411,840 B1 | 6/2002 | Bardy | |
| 6,416,471 B1 | 7/2002 | Kumar et al. | |
| 6,441,747 B1 | 8/2002 | Khair et al. | |
| 6,443,890 B1 | 9/2002 | Schulze et al. | |
| 6,450,953 B1 | 9/2002 | Place et al. | |
| 6,475,153 B1 | 11/2002 | Khair et al. | |
| 6,493,747 B2 | 12/2002 | Simmon et al. | |
| 6,494,829 B1 | 12/2002 | New, Jr. et al. | |
| 6,496,705 B1 | 12/2002 | Ng et al. | |
| 6,497,656 B1 | 12/2002 | Evans et al. | |
| 6,517,497 B2 | 2/2003 | Rymut et al. | |
| 6,533,729 B1 | 3/2003 | Khair et al. | |
| 6,540,686 B2 | 4/2003 | Heikkilä et al. | |
| 6,544,173 B2 | 4/2003 | West et al. | |
| 6,544,174 B2 | 4/2003 | West et al. | |
| 6,551,252 B2 | 4/2003 | Sackner et al. | |
| 6,559,620 B2 | 5/2003 | Zhou et al. | |
| 6,569,094 B2 | 5/2003 | Suzuki et al. | |
| 6,575,902 B1 | 6/2003 | Burton | |
| 6,577,893 B1 | 6/2003 | Besson et al. | |
| 6,579,231 B1 | 6/2003 | Phipps | |
| 6,589,170 B1 | 7/2003 | Flach et al. | |
| 6,593,528 B2 | 7/2003 | Franklin-Lees et al. | |
| 6,594,511 B2 | 7/2003 | Stone et al. | |
| 6,595,929 B2 | 7/2003 | Stivoric et al. | |
| 6,600,421 B2 | 7/2003 | Freeman | |
| 6,602,191 B2 | 8/2003 | Quy | |
| 6,603,401 B1 | 8/2003 | Ueyama | |
| 6,605,038 B1 | 8/2003 | Teller et al. | |
| 6,611,705 B2 | 8/2003 | Hopman et al. | |
| 6,612,984 B1 | 9/2003 | Kerr, II | |
| 6,616,606 B1 | 9/2003 | Petersen et al. | |
| 6,640,246 B1 | 10/2003 | Gary, Jr. et al. | |
| 6,659,947 B1 | 12/2003 | Carter et al. | |
| 6,669,630 B1 | 12/2003 | Joliat et al. | |
| 6,671,563 B1 | 12/2003 | Engelson et al. | |
| 6,694,180 B1 | 2/2004 | Boesen | |
| 6,723,046 B2 | 4/2004 | Lichtenstein et al. | |
| 6,731,989 B2 | 5/2004 | Engleson et al. | |
| 6,736,759 B1 | 5/2004 | Stubbs et al. | |
| 6,740,033 B1 | 5/2004 | Olejniczak et al. | |
| 6,748,250 B1 | 6/2004 | Berman et al. | |
| 6,749,566 B2 | 6/2004 | Russ | |
| 6,758,812 B2 | 7/2004 | Lang | |
| 6,773,396 B2 | 8/2004 | Flach et al. | |
| 6,817,979 B2 | 11/2004 | Nihtilä et al. | |
| 6,819,247 B2 | 11/2004 | Birnbach et al. | |
| 6,823,036 B1 | 11/2004 | Chen | |
| 6,840,904 B2 | 1/2005 | Goldberg | |
| 6,870,466 B2 | 3/2005 | Rust | |
| 6,871,211 B2 | 3/2005 | Labounty et al. | |
| 6,875,174 B2 | 4/2005 | Braun et al. | |
| 6,876,303 B2 | 4/2005 | Reeder et al. | |
| 6,893,396 B2 | 5/2005 | Schulze et al. | |
| 6,897,788 B2 | 5/2005 | Khair et al. | |
| 6,915,170 B2 | 7/2005 | Engleson et al. | |
| 6,937,150 B2 | 8/2005 | Medema et al. | |
| 6,942,616 B2 | 9/2005 | Kerr, II | |
| 6,984,297 B2 | 1/2006 | Nisch et al. | |
| 6,987,965 B2 | 1/2006 | Ng et al. | |
| 6,988,989 B2 | 1/2006 | Weiner et al. | |
| 7,002,468 B2 | 2/2006 | Eveland et al. | |
| 7,004,907 B2 | 2/2006 | Banet et al. | |
| 7,010,337 B2 | 3/2006 | Furnary et al. | |
| 7,020,508 B2 | 3/2006 | Stivoric et al. | |
| 7,029,455 B2 | 4/2006 | Flaherty | |
| 7,053,767 B2 | 5/2006 | Petite et al. | |
| 7,053,831 B2 | 5/2006 | Dempsey et al. | |
| 7,088,233 B2 | 8/2006 | Menard | |
| 7,099,895 B2 | 8/2006 | Dempsey | |
| 7,103,407 B2 | 9/2006 | Hjelt et al. | |
| 7,104,955 B2 | 9/2006 | Bardy | |

(56) References Cited

U.S. PATENT DOCUMENTS

| | | |
|---|---|---|
| 7,107,106 B2 | 9/2006 | Engleson et al. |
| 7,117,041 B2 | 10/2006 | Engleson et al. |
| 7,123,149 B2 | 10/2006 | Nowak et al. |
| 7,127,261 B2 | 10/2006 | Van Erlach |
| 7,129,836 B2 | 10/2006 | Lawson et al. |
| 7,130,396 B2 | 10/2006 | Rogers et al. |
| 7,138,902 B2 | 11/2006 | Menard |
| 7,153,262 B2 | 12/2006 | Stivoric et al. |
| 7,153,263 B2 | 12/2006 | Carter et al. |
| 7,154,398 B2 | 12/2006 | Chen et al. |
| 7,156,807 B2 | 1/2007 | Carter et al. |
| 7,171,166 B2 | 1/2007 | Ng et al. |
| 7,197,357 B2 | 3/2007 | Istvan et al. |
| 7,197,492 B2 | 3/2007 | Sullivan |
| 7,215,991 B2 | 5/2007 | Besson et al. |
| 7,222,054 B2 | 5/2007 | Geva |
| 7,231,258 B2 | 6/2007 | Moore et al. |
| 7,242,308 B2 | 7/2007 | Ulrich et al. |
| 7,256,708 B2 | 8/2007 | Rosenfeld et al. |
| 7,272,428 B2 | 9/2007 | Hopman et al. |
| 7,277,758 B2 | 10/2007 | DiLorenzo |
| 7,283,423 B2 | 10/2007 | Holm et al. |
| 7,292,135 B2 | 11/2007 | Bixler et al. |
| 7,292,139 B2 | 11/2007 | Mazar et al. |
| 7,294,105 B1 | 11/2007 | Islam |
| 7,301,451 B2 | 11/2007 | Hastings |
| 7,304,580 B2 | 12/2007 | Sullivan et al. |
| 7,319,386 B2 | 1/2008 | Collins, Jr. et al. |
| 7,324,824 B2 | 1/2008 | Smith et al. |
| 7,336,563 B2 | 2/2008 | Holm |
| 7,352,652 B2 | 4/2008 | Holm et al. |
| 7,362,656 B2 | 4/2008 | Holm |
| 7,384,110 B2 | 6/2008 | Hoshiyama et al. |
| 7,443,302 B2 | 10/2008 | Reeder et al. |
| 7,454,885 B2 | 11/2008 | Lin et al. |
| 7,480,951 B2 | 1/2009 | Weismiller et al. |
| 7,920,061 B2 | 4/2011 | Klein et al. |
| 8,026,821 B2 | 9/2011 | Reeder et al. |
| 8,258,965 B2 | 9/2012 | Reeder et al. |
| 8,487,774 B2 | 7/2013 | Reeder et al. |
| 2001/0034475 A1 | 10/2001 | Flach et al. |
| 2002/0103674 A1 | 8/2002 | Reeder et al. |
| 2002/0165731 A1 | 11/2002 | Dempsey |
| 2002/0198986 A1 | 12/2002 | Dempsey |
| 2003/0141981 A1 | 7/2003 | Bui et al. |
| 2004/0072475 A1 | 4/2004 | Istvan |
| 2004/0073127 A1 | 4/2004 | Istvan et al. |
| 2004/0121767 A1 | 6/2004 | Simpson et al. |
| 2004/0127802 A1 | 7/2004 | Istvan et al. |
| 2004/0147818 A1 | 7/2004 | Levy et al. |
| 2004/0167465 A1 | 8/2004 | Mihai et al. |
| 2004/0176667 A1 | 9/2004 | Mihai et al. |
| 2005/0140508 A1 | 6/2005 | Tessier et al. |
| 2005/0148303 A1 | 7/2005 | Dempsey |
| 2005/0168341 A1 | 8/2005 | Reeder et al. |
| 2005/0177052 A1 | 8/2005 | Istvan et al. |
| 2005/0197545 A1 | 9/2005 | Hoggle |
| 2005/0206518 A1 | 9/2005 | Welch et al. |
| 2005/0251002 A1 | 11/2005 | Istvan et al. |
| 2005/0251003 A1 | 11/2005 | Istvan et al. |
| 2005/0251004 A1 | 11/2005 | Istvan et al. |
| 2006/0030759 A1 | 2/2006 | Weiner et al. |
| 2006/0077759 A1 | 4/2006 | Holm |
| 2006/0089539 A1 | 4/2006 | Miodownik et al. |
| 2006/0106649 A1 | 5/2006 | Eggers et al. |
| 2006/0122867 A1 | 6/2006 | Eggers et al. |
| 2006/0136271 A1 | 6/2006 | Eggers et al. |
| 2006/0143051 A1 | 6/2006 | Eggers et al. |
| 2006/0190302 A1 | 8/2006 | Eggers et al. |
| 2006/0214786 A1 | 9/2006 | Bixler et al. |
| 2006/0220839 A1 | 10/2006 | Fifolt et al. |
| 2006/0238350 A1 | 10/2006 | Tessier |
| 2006/0239195 A1 | 10/2006 | Camins et al. |
| 2006/0242293 A1 | 10/2006 | Russ |
| 2006/0248221 A1 | 11/2006 | Hottel et al. |
| 2006/0253281 A1 | 11/2006 | Letzt et al. |
| 2006/0258926 A1 | 11/2006 | Ali et al. |
| 2006/0267740 A1 | 11/2006 | Bixler et al. |
| 2006/0277202 A1 | 12/2006 | Dempsey |
| 2006/0279427 A1 | 12/2006 | Becker et al. |
| 2006/0288095 A1 | 12/2006 | Torok et al. |
| 2007/0013511 A1 | 1/2007 | Weiner et al. |
| 2007/0060976 A1 | 3/2007 | Denzene et al. |
| 2007/0069887 A1 | 3/2007 | Welch et al. |
| 2007/0112602 A1 | 5/2007 | Bellon et al. |
| 2007/0123955 A1 | 5/2007 | Verhoef et al. |
| 2007/0135866 A1 | 6/2007 | Baker et al. |
| 2007/0142716 A1 | 6/2007 | Biondi |
| 2007/0156456 A1 | 7/2007 | McGillin et al. |
| 2007/0156707 A1 | 7/2007 | Fuchs et al. |
| 2007/0180140 A1 | 8/2007 | Welch et al. |
| 2007/0208235 A1 | 9/2007 | Besson et al. |
| 2007/0229249 A1 | 10/2007 | McNeal et al. |
| 2007/0233199 A1 | 10/2007 | Moore et al. |
| 2007/0251835 A1 | 11/2007 | Mehta et al. |
| 2007/0255111 A1 | 11/2007 | Baldus et al. |
| 2007/0255250 A1 | 11/2007 | Moberg et al. |
| 2007/0255348 A1 | 11/2007 | Holtzclaw |
| 2007/0258395 A1 | 11/2007 | Jollota et al. |
| 2007/0279211 A1 | 12/2007 | Fenske et al. |
| 2008/0009694 A1 | 1/2008 | Hopman et al. |
| 2008/0018435 A1 | 1/2008 | Brown |
| 2008/0049555 A1 | 2/2008 | Holm et al. |
| 2008/0114689 A1 | 5/2008 | Psynik et al. |
| 2008/0120784 A1 | 5/2008 | Warner et al. |
| 2008/0122616 A1 | 5/2008 | Warner et al. |
| 2008/0126122 A1 | 5/2008 | Warner et al. |
| 2008/0126132 A1 | 5/2008 | Warner et al. |
| 2008/0147442 A1 | 6/2008 | Warner et al. |
| 2009/0096615 A1 | 4/2009 | Reeder et al. |

OTHER PUBLICATIONS

Priyantha, et al., "The Cricket Location-Support System," ACM MOBICOM, Aug. 2000.

Chakraborty, Anit, "A Distributed Architecture for Mobile, Location-Dependent Applications," Massachusetts Institute of Technology (1999).

* cited by examiner

SYSTEM FOR MONITORING CAREGIVERS AND EQUIPMENT

REFERENCE TO PRIORITY APPLICATIONS

This application is a continuation of U.S. application Ser. No. 13/599,110, filed Aug. 30, 2012, now U.S. Pat. No. 8,487,774, which is a continuation of U.S. application Ser. No. 13/238,899, filed Sep. 21, 2011, now U.S. Pat. No. 8,258,965, which is a continuation of U.S. application Ser. No. 12/258,058, filed Oct. 24, 2008, now U.S. Pat. No. 8,026,821, which is a continuation of U.S. application Ser. No. 11/075,979, filed Mar. 9, 2005, now U.S. Pat. No. 7,443,302, which is a continuation of U.S. application Ser. No. 09/849,688, filed May 4, 2001, now U.S. Pat. No. 6,876,303, which claims the benefit of U.S. Provisional Application No. 60/202,283, entitled "Patient Point of Care Computer System," filed May 5, 2000, and U.S. Provisional Application No. 60/202,284, entitled "Remote Control for a Hospital Bed," filed May 5, 2000, and U.S. Provisional Application No. 60/229,136, entitled "Patient Point of Care Computer System," filed Aug. 30, 2000, all of which are hereby incorporated herein by reference.

CROSS REFERENCE TO RELATED APPLICATIONS

The disclosures of related U.S. Nonprovisional application Ser. No. 09/849,580, entitled "Patient Point of Care Computer System", filed May 4, 2001, and U.S. Nonprovisional application Ser. No. 09/848,941, entitled "Remote Control for a Hospital Bed" filed May 4, 2001 are incorporated herein by reference.

BACKGROUND AND SUMMARY OF THE INVENTION

The present invention relates to a hospital monitoring system, and more particularly, to hospital monitoring system for monitoring hospital personnel, a plurality of patient locations for patients, and associated devices.

Hospital staff, including doctors, nurses, physician assistants, orderlies, etc., provide patient care while the patient is undergoing treatment and/or therapy during a hospital visit. A number of systems have been developed to facilitate providing patient care, such as personnel locating systems, nurse call systems, bed status information systems, and patient monitoring devices. Details of such systems are disclosed in U.S. Pat. Nos. 6,067,019 (Bed Exit Detection Apparatus); 5,838,223 (Patient/Nurse Call System); 5,808,552 (Patient Detection System for a Patient-Support Device); 5,699,038 (Bed Status Information System for Hospital Beds); 5,561,412 (Patient/Nurse Call System); and 5,537,095 (Incontinence Detection Device), the disclosures of which are incorporated herein by reference. Additionally, co-pending U.S. Nonprovisional application Ser. No. 09/849,580, filed May 4, 2001, entitled "Patient Point of Care Computer System," and 09/848,941, filed May 4, 2001, entitled "Remote Control For a Hospital Bed," the disclosures of which are incorporated herein by reference, also disclose systems that have been developed to facilitate providing patient care.

The systems disclosed above facilitate various patient alarms, such as a patient exiting a bed, an incontinence event, or an emergency call for a caregiver. Typically, a caregiver will enter the patient's room when responding to an alarm. However, the caregiver often must manually silence the alarm, adjust the room lighting, or shut off a television or radio prior to attending to the patient. This manual preparation of the working environment may distract the caregiver and further increases response time to critical alarms. The disclosure is directed toward the automatic silencing of such alarms and/or preparing the working environment when a responsive caregiver enters the patient's room. Further, the disclosure is directed toward preparing the working environment when an alarm is received. Further still, the disclosure is directed toward preparing the working environment when an alarm is received, subject to environmental and patient control overrides depending on the nature of the alarm and time of the alarm.

The system disclosed also provides for automatic lockouts of patient and environmental controls when the caregiver enters the room, regardless of the presence of an alarm. As a caregiver makes his or her rounds, the caregiver may need to tend to the patient's needs. Often a caregiver must ensure that patient activated controls are locked out during this time, as the patient may inadvertently activate a control and interfere with the caregiver's duties. Also disclosed is a system that provides for the automatic enablement of patient controls, bed controls, and/or environmental controls when a caregiver is in the room.

One illustrative embodiment prevents the status of bed lockouts from being changed without an authorized caregiver within the room. When the caregiver enters the room, the system receives a caregiver identification signal from a caregiver badge. After the system authenticates the identification signal, the system then permits the bed lockout status to be changed. The bed lockout controls prevent the patient on bed from actuating certain controls. These lockouts are typically actuated by pressing a button or a combination of two or more buttons on the bed to lock out various bed controls, environmental controls, or other functions.

Another embodiment is designed for use with beds which are movable from a generally flat bed position to a chair position. In this embodiment of the present invention, the bed is unable to move to a chair position unless an authorized caregiver is located within the room. Again, the system must receive and authenticate the identification signal from caregiver badge before the bed is permitted to move to the chair position.

In yet another embodiment, the status of patient environmental controls adjacent a bed is automatically altered when the caregiver enters the room. For example, in one embodiment the sound on a TV/radio device is muted and specific light sources are activated when the caregiver enters the room. A system receives the caregiver identification signal. After the system authenticates the identification signal, the system instructs the TV/radio device to mute all sound and the light source to activate specific lights. In another embodiment, the system locks out one or more of the environmental controls within the room once the control unit authenticates the identification signal from the caregiver badge. Therefore, the patient can no longer control the environmental functions such as, for example, the radio, television or lighting when an authorized caregiver is in the room.

According to the invention, a hospital monitoring system for monitoring hospital personnel, a plurality of patient locations for patients, and associated devices is disclosed. The system comprises a plurality of transmitters carried by hospital personnel, each transmitter periodically transmitting a transmitter signal unique to that transmitter; a plurality of receivers, each receiver corresponding to a patient location, the receivers receiving the transmitter signals and outputting a receiver signal; and a computer coupled to the associated devices, the computer configured to receive the receiver signals and determine the presence of hospital personnel in the patient locations, the computer further configured to alter device states based on the presence of hospital personnel.

Also according to the invention, a method of controlling devices in a patient location is provided. The method comprises the steps of associating the patient location to a patient; associating devices to the patient location; determining the presence of hospital personnel in the patient location; and altering the state of the devices based the presence of hospital personnel.

Also according to the invention, a hospital monitoring system for monitoring hospital personnel, a plurality of patient locations for patients, and associated devices is provided. The system comprises a locating and tracking system configured to locate and track hospital personnel located in the plurality of patient locations; a computer coupled to the associated devices and the locating and tracking system, the computer configured to determine the presence of hospital personnel in the patient locations from the locating and tracking system, the computer further configured to alter device states based on the presence of hospital personnel. The computer also includes a database, the database comprising a patient database, the patient database associated each patient with a patient location; a hospital personnel database, the hospital personnel database associating each hospital personnel with a caregiver or non-caregiver class, the hospital personnel database further associating hospital personnel with a patient; and an alarm database, the alarm database associating a plurality of alarms with the hospital personnel.

Additional features of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
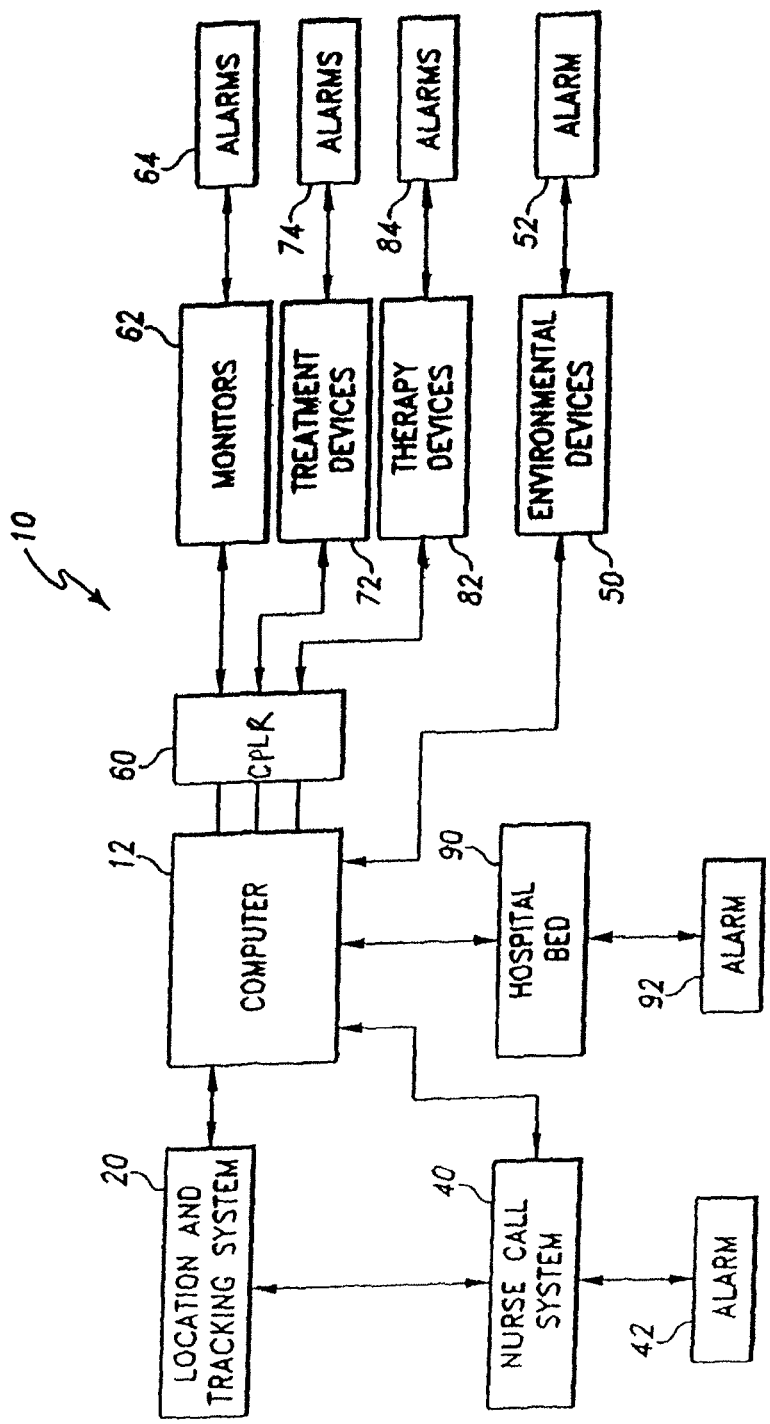
FIG. 1 is a block diagram illustrating the components of the hospital monitoring and control system of the present invention.
Figure 2:
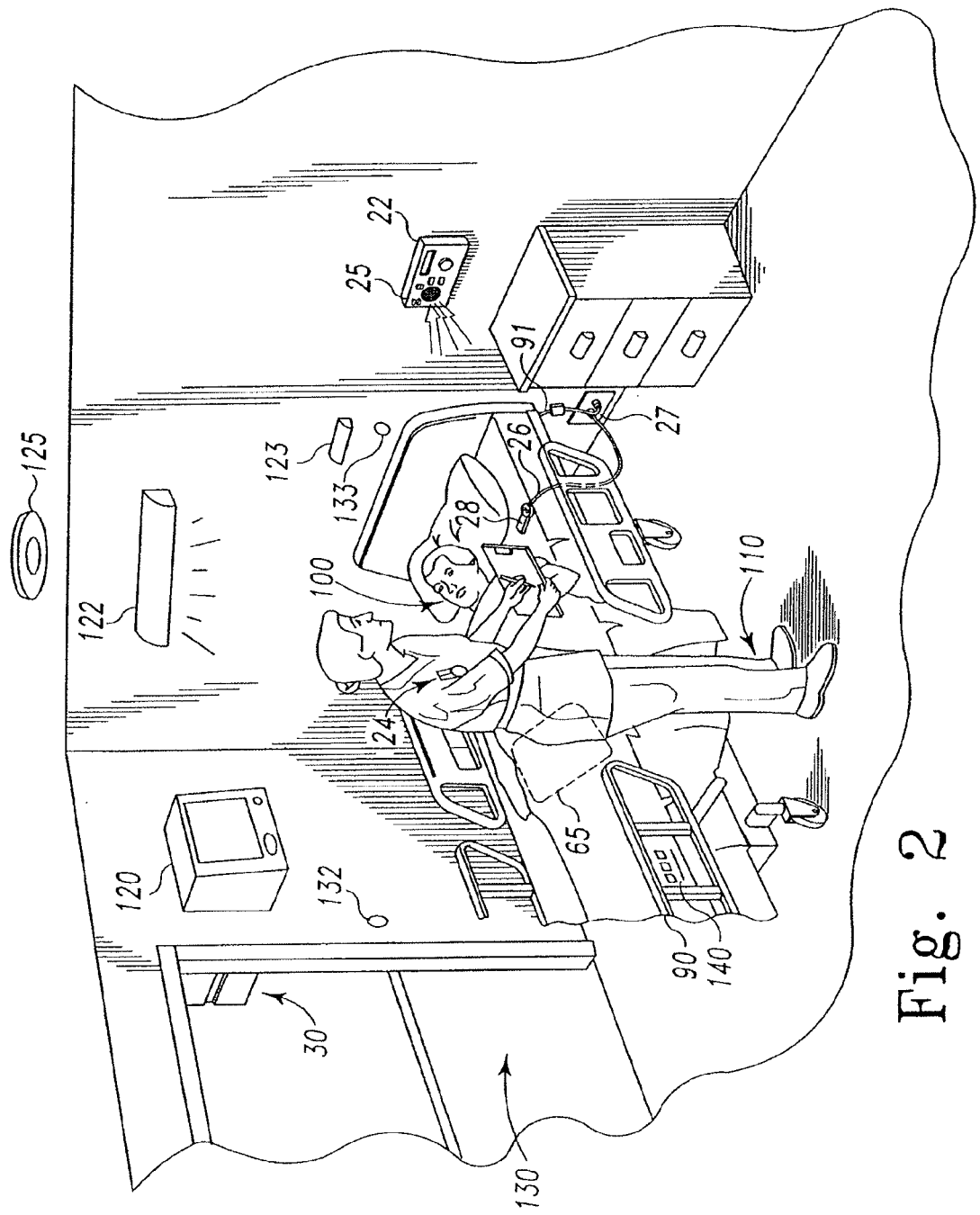
FIG. 2 is a perspective view of a portion of a hospital room which illustrates a patient station in a patient room and the physical arrangement of other components, including an incontinence detection device.

Referring now to the drawings, FIGS. 1 and 2 illustrates a block diagram of the hospital monitoring and control system 10 of the present invention, and an illustrative hospital environment in which the system is utilized.

FIG. 2 illustrates a patient room 130 which includes a patient station 22 and the physical arrangement of other components, including an incontinence detection device 65. The patient station 22 is illustratively a component of a nurse call system 40. Caregiver 110 wears a badge 24 which clips to the caregiver's 110 clothing. The badge 24 transmits a pulse-coded signal, preferably infrared or RF, which is received by receiver 25, which is preferably located at the patient station 22, and/or an overhead receiver 125 so that the location and tracking systems 20 can determine and continuously update locations of caregivers 110 on duty. Overhead light 122 provides room illumination, and reading light 123 provides reading illumination for the patient. Overhead light 122 and reading light 123 are controlled by light controls 132 and 133, respectively.

Pillow unit 28 connects via a cable 26 to a receptacle 27 which, in turn, is connected to the nurse call system 40. Pillow unit 28 allows the patient 100 to manually place a nurse call or alarm via nurse call system 40. Pillow unit also allows patient 100 access to bed 90 controls and environmental controls 50. Bed 90 controls are also accessible by the caregiver 110 via control panel 140.

Incontinence detection device 65 is interposed between the bed 90 and patient 110. Incontinence detection device 65 is connected to the computer 12 via bed 90 electronics and cable 91 via receptacle 27.

The system 10 illustratively includes a computer 12 configured to monitor various system alarms, device status, the hospital personnel information, and patient information. Computer 12 is coupled to a location and tracking system 20. Location and tracking system 20 monitors and tracks the location of hospital personnel, patients and equipment within the hospital. Computer 12 is also connected to nurse call system 40. Nurse call system 40 is associated with various alarms 42. The alarms 42 illustratively include the following:

| ALARM | PRIORITY | GENERATED BY |
|---|---|---|
| Code Blue | 1 | Human/Input Device |
| Staff Emergency | 2 | Human/Input Device |
| Bathroom | 3 | Human/Input Device |
| Shower | 4 | Human/Input Device |
| Patient Equipment | 5 | Automatic/Input Device |

Illustratively, the alarms 42 will place a call to a caregiver through location and tracking system 20 and nurse call system 40.

Computer 12 is also connected to hospital bed 90. Hospital bed 90 is associated with alarms 92. Alarms 92 include bed malfunction alarms and/or bed exit alarms, and incontinence detection device 65 alarms. Illustratively, alarms 92 will place a call to a caregiver through location and tracking system 20 and nurse call system 40.

Figure 14:
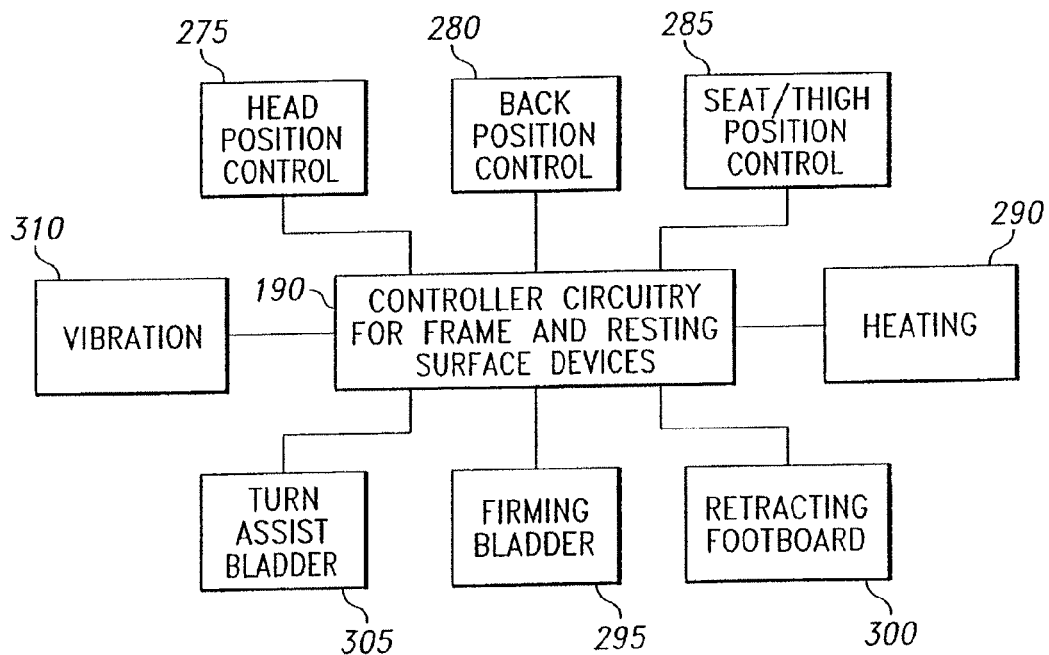
FIG. 14 is a block diagram illustrating the bed controller and associated bed controls.

Bed 90 includes frame and resting surface devices 190 adjust the position of bed 90 and the position and shape of the resting surface, as illustrated in FIG. 14. In addition, other devices are included in frame and resting surface devices 190, such as resting surface vibration, temperature and firmness controls. Caregiver 110 accesses and changes the state of frame and resting surface devices 190 via control panel 140, shown in FIG. 2. FIG. 14 shows several frame and resting surface devices 190, however FIG. 14 should not be considered an exhaustive list. Examples of frame and resting surface devices 190 include head position control 275, back position control 280, seat/thigh position control 285, heating control 290, firming bladder 295, retracting footboard control 300, turn assist bladder control 305 and vibration control 310.

Head position control 275, back position control 280 and seat/thigh position control 285 all alter the shape of the resting surface of bed 90. Head position control 275 raises or lowers the head position of the resting surface generally coincident with the head of the patient. Back position control 280 raises or lowers the middle portion of the resting surface generally coincident with the back of the patient. Seat/thigh position control 285 raises or lowers the lower portion of the resting surface generally coincident with the seat and thighs of a patient.

Heating control 290 controls the temperature of the resting surface of bed 90. Similarly, vibration control 310 controls the vibratory action of the resting surface of bed 90. Firming bladder control 295 controls the firmness of the resting surface of bed 90. Retracting footboard control 300 adjusts the length of the foot portion of the resting surface of bed 90. This allows bed 90 to accommodate patients of various heights comfortably. Turn assist bladder control 305 controls rotation of the patient to reduce the likelihood of pulmonary complications. An interface pressure sensor and controller for a patient support surface such as an air mattress may also be coupled to the controller 190.

Computer 12 is also connected to coupler 60. The computer 12 may be coupled to monitors 26, treatment devices 72, and therapy devices 82 through coupler 60. Illustratively, coupler 60 may be an RS-232 compatible cable or other suitable connector, such as a RS-485 compatible cable, Ethernet, or other network connection device known to those of ordinary skill in the art. Computer 12 processes signals from the monitors 62, treatment devices 72, and therapy devices 82 on a real time basis. The monitors 62, treatment devices 72, and therapy devices 82 include, but are not limited to, heart rate monitors, temperature sensors, blood pressure monitors (invasive and noninvasive), EKG monitors, blood oxygen sensors, capnographs, ventilators, IV pumps, scales, chest drainage monitors, and the like. Monitors 62, treatment devices 72 and therapy devices 82 have associated alarms 64, 74 and 84, respectively. Illustratively, alarms 64, 74, and 84 will place a call to a caregiver through location and tracking system 20 and nurse call system 40.

Computer 12 is also connected to environmental devices 50. Alarm 52 is associated with environmental devices 50. Environmental devices 50 illustratively include temperature control devices, such as a thermostat, and humidity control devices, such as a humidifier. Additionally, environmental devices 50 illustratively include entertainment devices such as a television/radio 120, and lighting such as overhead light 122 and reading light 123, all of which do not have alarms associated therewith.

Figure 13:
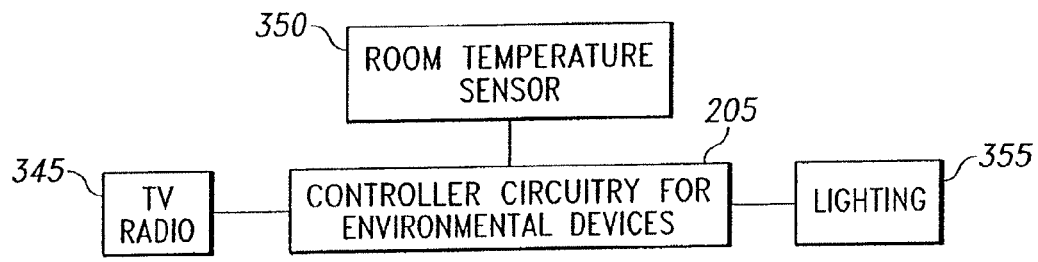
FIG. 13 is a block diagram illustrating the control circuitry for several environmental controls.

Environmental devices 50 control environmental parameters within the patient room. FIG. 13 shows several different environmental devices 50; however FIG. 13 should not be considered an exhaustive list. Examples of environmental devices 50 include TV/radio 120 control 345, room temperature control 350 and lighting control 355, which control overhead light 122 and reading light 123.

TV/radio 120 control 345 controls the functions of the TV/radio 120 in the room. Room temperature control 350 is a thermostat control for altering the temperature of the patient's room. Lighting control 355 controls overhead light 122 and reading light 123, and their brightness level.

In one embodiment, the status of the environmental controls is automatically altered when caregiver 110 enters the room. For example, the sound on TV/radio 120 is muted and overhead light 122 and/or reading light 123 controlled by lighting control 355 are activated. When caregiver 110 enters the room, receiver 25 receives the caregiver identification signal broadcast by caregiver badge 24. After the computer 12 authenticates the identification signal, the computer 12 instructs TV/radio 120 control 345 to mute all sound and lighting device 355 to illuminate overhead light 122 and reading light 123.

In another embodiment of the present invention, the computer 12 overrides one or more of the environmental controls within the room once the computer 12 authenticates the identification signal from the badge 24. In other words, the patient can no longer control the environmental functions such as, for example, the radio, television or lighting when an authorized caregiver 110 is in the room.

Bed 90 includes lockout controls which prevent the patient 100 on bed 90 from actuating certain controls. These lockouts are typically actuated by pressing a button or a combination of two or more buttons on the bed to lock out various bed controls, environmental controls, or other functions. In one embodiment of the present invention, these bed lockouts cannot be changed without an authorized caregiver 110 within the room. In other words, when caregiver 110 enters the room, the receiver 25 receives the caregiver identification signal from the badge 24. After the control unit authenticates the identification signal 24, computer 12 then permits the bed lockout status to be changed.

Certain beds such as the TotalCare® bed available from Hill-Rom, Inc. are capable of moving from a generally flat bed position to a chair position. In one embodiment of the present invention, the bed is unable to move to a chair position unless an authorized caregiver 110 is located within the room. Again, the computer 12 must receive and authenticate the identification signal from badge 24 before the bed is permitted to move to the chair position. Thus, a feature is selectively locked out in the absence of a caregiver 110.

Figure 15:
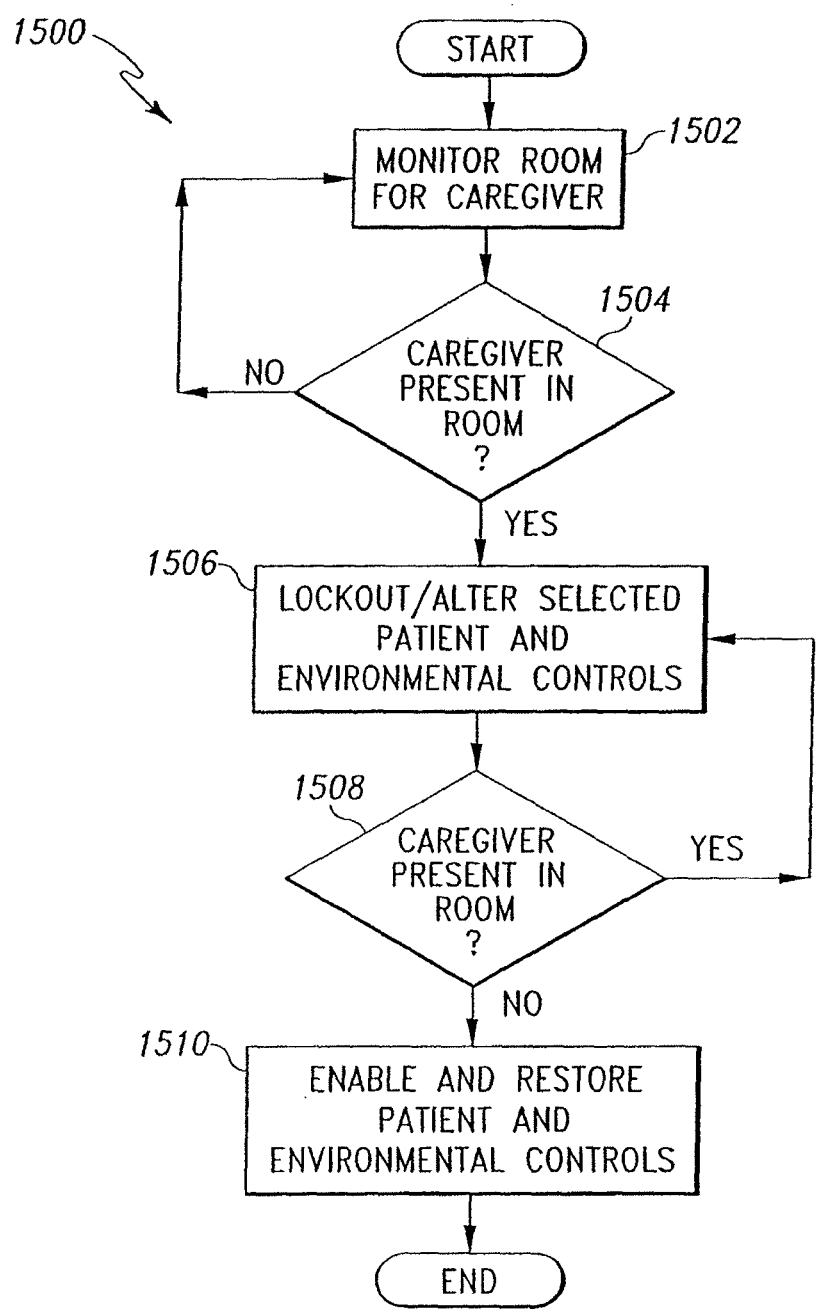
FIG. 15 is a flow chart of another illustrative embodiment describing a process which lockouts and/or alters selected patient and environmental controls when a caregiver is present in the room.

FIG. 15 depicts shows a flow chart 1500 of the illustrative embodiments, and describes a process which lockouts and/or alters selected patient and environmental controls when a caregiver 110 is present in the room. In step 1502, the locating and tracking system 20 monitors the room for a caregiver 110. If a caregiver enters the room, step 1504 exits the monitoring loop and enables step 1506, which locks out and/or alters selected patient and environmental controls. In step 1508, the locating and tracking system 20 monitors the room for the presence of the caregiver 110 and retains the state of 1506 as long as the caregiver 110 is in the room. When the caregiver 110 exits the room, the patient lockouts are removed and the environment is restored, along with the patient 100 controls to alter the environment.

Figure 16:
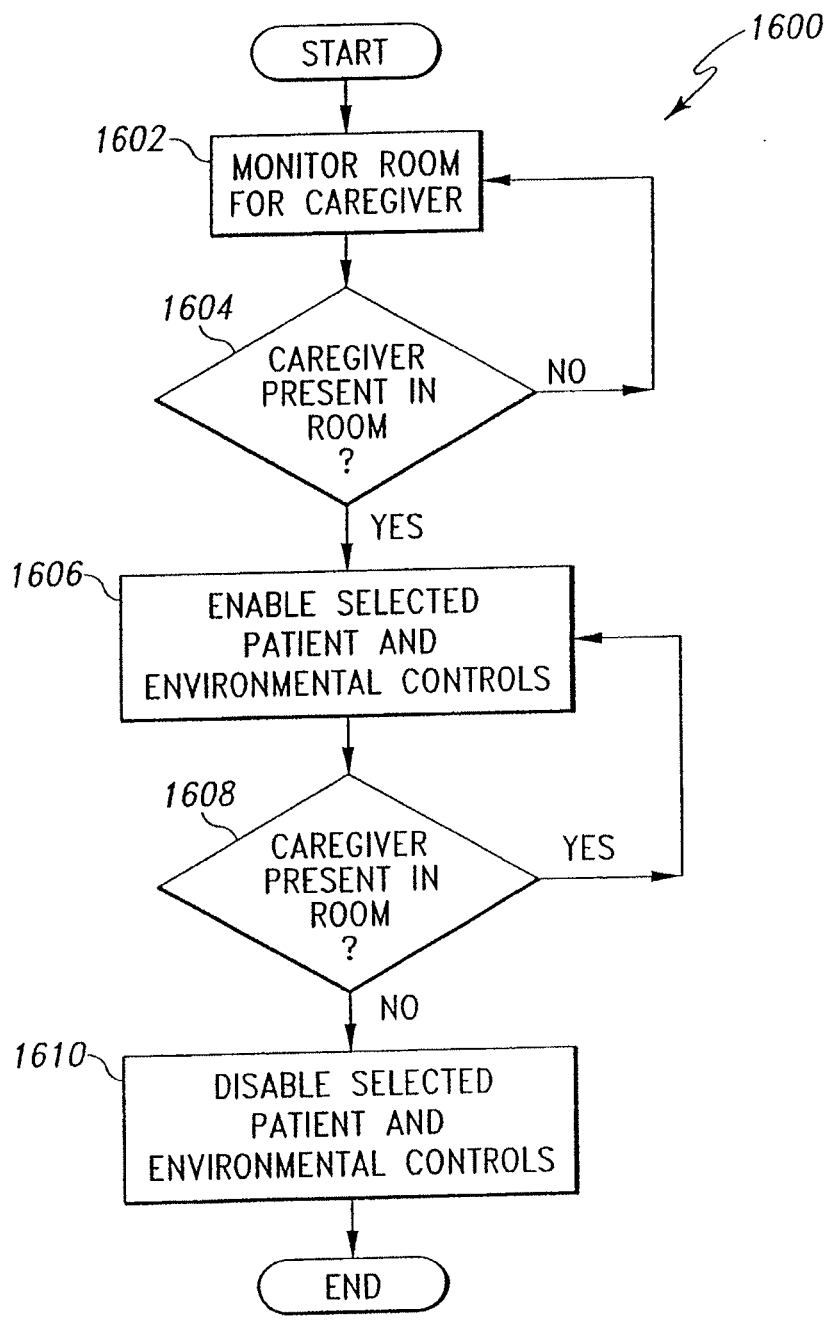
FIG. 16 is a flow chart of another illustrative embodiment describing a process which enables selected patient and environmental controls when a caregiver is present the room.

FIG. 16 depicts shows a flow chart 1600 of another one of the illustrative embodiments, and describes a process which enables and/or alters selected patient and environmental controls when a caregiver 110 enters the room. In step 1602, the locating and tracking system 20 monitors the room for a caregiver 110. If a caregiver enters the room, step 1604 exits the monitoring loop and enables step 1606, which enables and/or alters selected patient and environmental controls. In step 1608, the locating and tracking system 20 monitors the room for the presence of the caregiver 110 and retains the state of 1606 as long as the caregiver 110 is in the room. When the caregiver 110 exits the room, the patient and environmental lockouts are restored.

Figure 3:
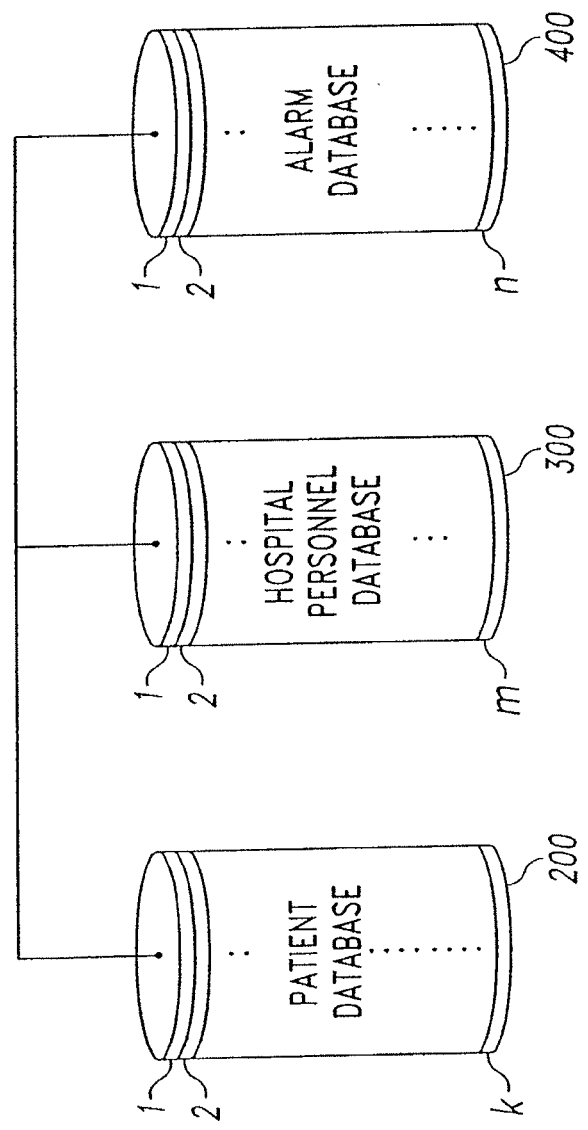
FIG. 3 depicts a database structure used to associate patients with hospital personnel, and associate hospital personnel with alarms.

FIG. 3 depicts a database structure used to associate patients with hospital personnel, and associate hospital personnel with alarms. Patient information is stored in patient database 200. As depicted in FIG. 3, there are numerous patients in the database, ranging from record number 1 to k.

Hospital personnel information is stored in hospital personnel database 300. There are numerous hospital personnel in the hospital personnel database 300, ranging from record number 1 to m. Furthermore, hospital personnel information stored in hospital personnel database 300 is categorized by personnel position. Illustratively, the hospital personnel database contains a "doctor" class, a "nurse" class, an "orderly" class, and a "non-caregiver" class. Non-caregiver class illustratively includes security staff, administrative staff, or janitorial staff.

Alarm database 400 stores alarm information for alarm records 1 to n, each record associated with a different alarm. Furthermore, alarm information stored in alarm database 300 includes alarm type and alarm priority. Thus, alarm record 1, for example, may be associated with a cardiac arrest and allocated priority 1, the highest priority and thus requiring immediate attention, and alarm record n may be associated with an incontinence event, and be allocated a lower priority.

Figure 4:
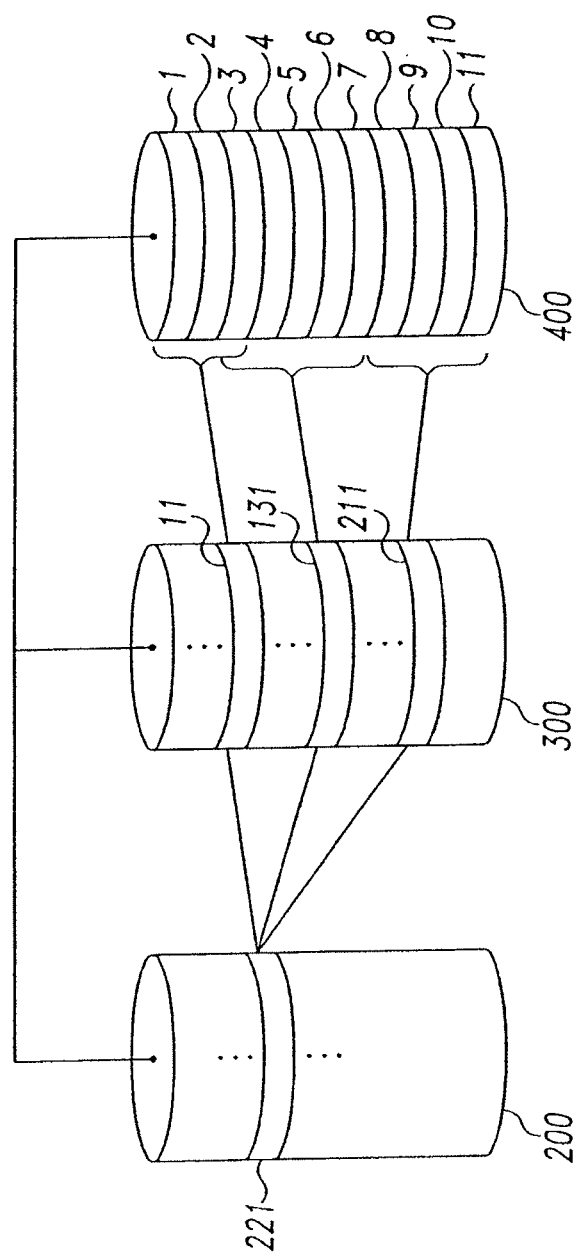
FIG. 4 depicts the database association for a specific patient record, the patient associated with hospital personnel, and the hospital personnel associated with alarms.

FIG. 4 depicts the database association for a specific patient record, the patient associated with hospital personnel, and the hospital personnel associated with alarms. Illustratively, patient record 221 is associated with hospital personnel records 11, 131, and 211. In the present example, the patient represented by patient record 221 has been admitted for a heart procedure requiring surgery. Hospital personnel records 11, 131, and 211 correspond to a surgeon, a cardiologist and a nurse, respectively. Alarms records 1-11 in alarm database 400 are associated with hospital personnel records 11, 131, and 211. In the illustrative example, alarm records 1-3 are associated with hospital personnel record 11, alarm records 3-7 are associated with hospital personnel record 131, and alarm records 8-11 are associated with hospital personnel record 211. Illustratively, alarm record 1 corresponds to a cardiac arrest, and has the highest priority, which requires the attention of a cardiologist. Alarm record 3 corresponds to a less severe cardiac event, such as an irregular heart rate, and thus has a lesser priority, and requires either the cardiologist or surgeon.

Figure 5:
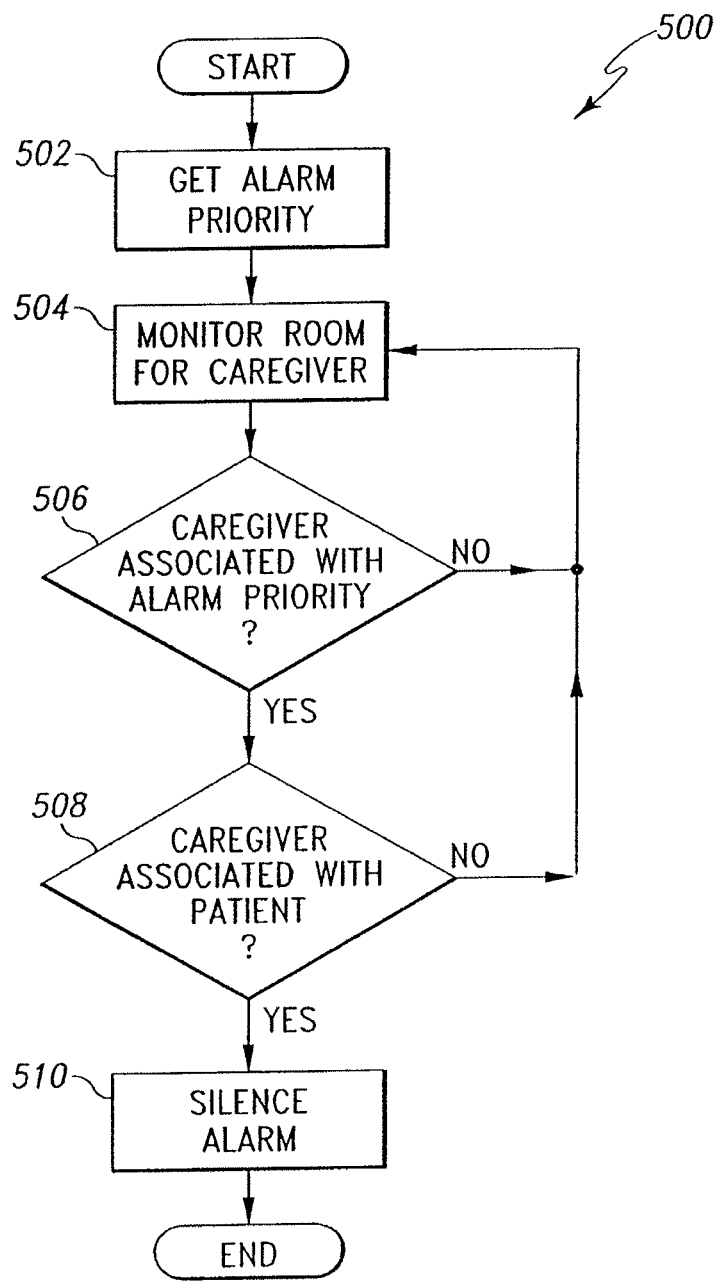
FIG. 5 is a flowchart of an illustrative embodiment of an automatic alarm silencing process that includes association of patients, hospital personnel and alarms.

The flow diagram 500 of FIG. 5 depicts one illustrative embodiment of the automatic alarm silencing process that includes association of patients, hospital personnel and alarms. In step 502, the computer 12 receives an alarm from either the location and tracking system 20, the nurse call system 40, a treatment device 72, a therapy device 82, environmental devices 50, or the hospital bed 90. Upon receiving the alarm signal, computer 12 gets the alarm priority from alarm database 400, and may also notify the caregiver at their current location. In step 504, the computer monitors the room 130 from which the alarm was received for a caregiver. In the illustrative embodiment disclosed herein, patient station 22 monitors the room 130 via receiver 25. Upon entering the room 130, a caregiver is identified by badge 24, which emits an infrared pulse and is detected by receiver 25. Computer 12 receives the caregiver identification and thus identifies the associated hospital personnel record in hospital personnel database 300.

In step 506, computer 12 determines whether the caregiver in room 130 is associated with the alarm priority stored in alarm database 400. For example, if the alarm priority is 3, indicating a cardiac event of lower priority than a cardiac arrest, and the person entering the room is identified as a non-caregiver, e.g., a security officer, the alarm will not be silenced. Similarly, if the caregiver is identified as a nurse, the alarm will not be silenced. Conversely, if the caregiver is identified as a cardiologist or surgeon, which in this example is associated with the alarm of priority 3, then step 508 determines if the doctor identified is associated with that patient. If the doctor is associated with the patient, then the alarm is silenced in step 510. If the doctor is not associated with the patient, the alarm is not silenced.

Figure 6:
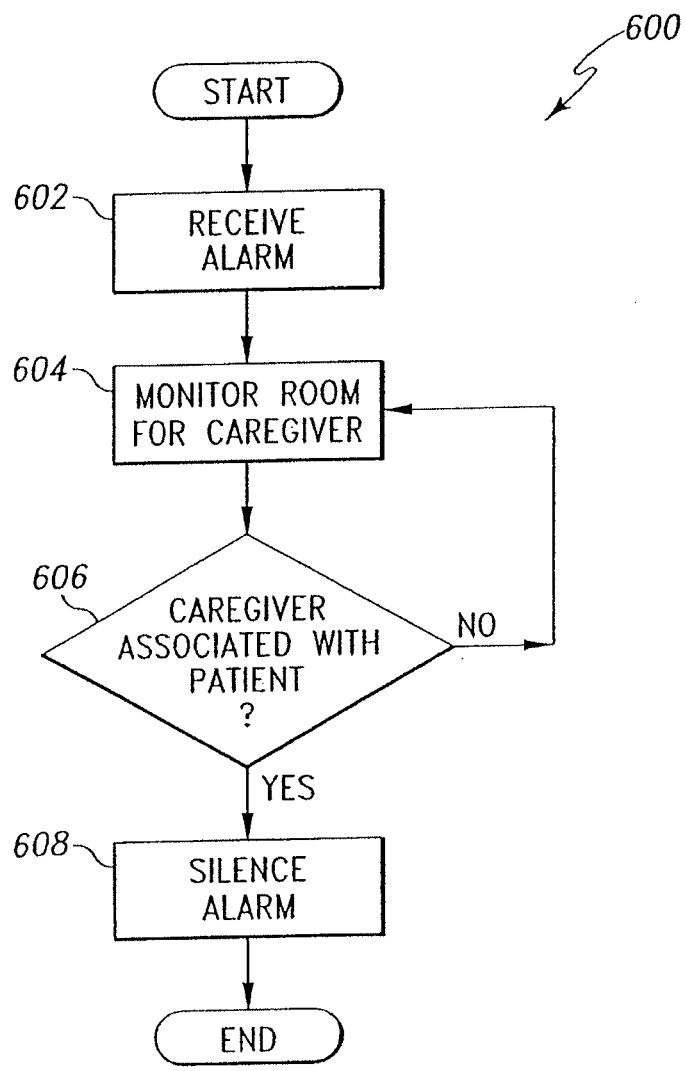
FIG. 6 is a flowchart of another illustrative embodiment of an automatic alarm silencing process that includes association of patients and hospital personnel.

The flow diagram 600 of FIG. 6 depicts another illustrative embodiment of the automatic alarm silencing process that includes associating patients with hospital personnel. In step 602, the computer 12 receives an alarm from either the location and tracking system 20, the nurse call system 40, a treatment device 72, a therapy device 82, environmental devices 50, or the hospital bed 90. Upon receiving the alarm signal, computer 12 monitors the room 130 from which the alarm was received for a caregiver, as shown in step 604. In the illustrative embodiment disclosed herein, patient station 22 monitors the room 130 via receiver 25. Upon entering the room 130, a caregiver is identified by badge 24, which emits an infrared and/or RF pulse and is detected by receiver 25. Computer 12 receives the caregiver identification and thus identifies the associated hospital personnel record in hospital personnel database 300. Step 606 determines if the caregiver is associated with the patient. If the caregiver is associated with the patient, then the alarm is silenced in step 608. If the caregiver is not associated with the patient, the alarm is not silenced.

Figure 7:
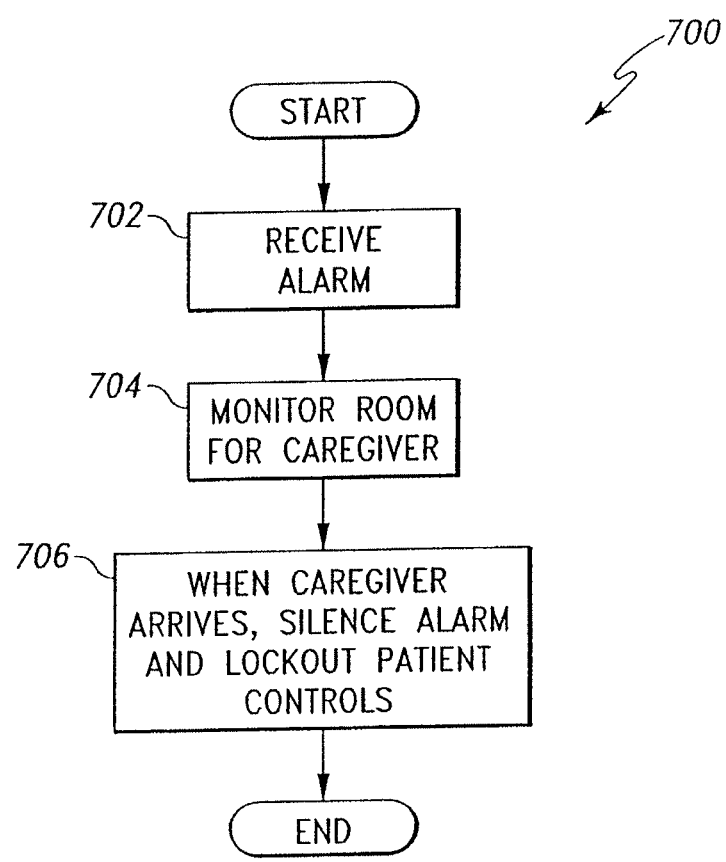
FIG. 7 is a flowchart of an illustrative embodiment of an alarm silencing process in conjunction with a patient control lockout that includes a lockout of patient activated controls.

The flow diagram 700 of FIG. 7 depicts another illustrative embodiment of the automatic alarm silencing process that includes a lockout of patient activated controls. In step 702, the computer 12 receives an alarm from either the location and tracking system 20, the nurse call system 40, a treatment device 72, a therapy device 82, environmental devices 50, or the hospital bed 90. Upon receiving the alarm signal, computer 12 monitors the room 130 from which the alarm was received for a caregiver, as shown in step 704. In the illustrative embodiment disclosed herein, patient station 22 monitors the room 130 via receiver 25. Upon entering the room 130, a caregiver is identified by badge 24, which emits an infrared pulse and is detected by receiver 25. Once the caregiver enters the room, step 706 silences the alarm and locks out any patient activated controls, such as bed 90 controls or television/radio 120 controls, thus decreasing the likelihood that the patient 100 may inadvertently interfere with caregiver 110 while the caregiver 110 administers the required therapy in response to the alarm.

Figure 8:
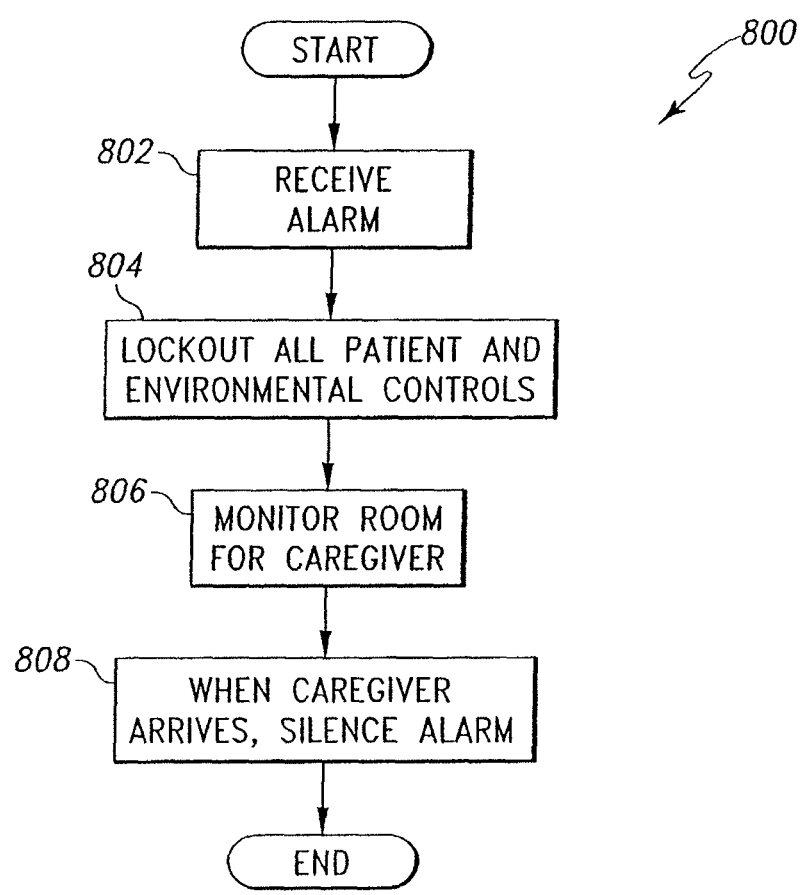
FIG. 8 is a flowchart of another illustrative embodiment of an automatic alarm silencing process in conjunction with a patient control lockout that includes a lockout of patient activated controls upon the occurrence of the alarm.

The flow diagram 800 of FIG. 8 depicts another illustrative embodiment of the automatic alarm silencing process in conjunction with a patient control lockout that includes a lockout of patient activated controls immediately upon the occurrence of an alarm. Locking out patient and environmental controls as soon as an alarm is received is desirable should the patient 100 be suffering from severe condition, such as a cardiac arrest or seizure, so as to prevent a patient s involuntary movement from accidentally activating a bed 90 or environmental devices 50.

In step 802, the computer 12 receives an alarm from either the location and tracking system 20, the nurse call system 40, a treatment device 72, a therapy device 82, environmental devices 50, or the hospital bed 90. Upon receiving the alarm signal, computer 12 immediately locks out all patient and environmental controls as shown in step 804. Controller 12 then monitors the room 130 from which the alarm was received for a caregiver, as shown in step 806. Once the caregiver enters the room, step 808 silences the alarm.

Often an alarm may sound when a caregiver 110 in present in the hospital room 130. In such a situation, it is not desirable to automatically cancel the alarm, as the caregiver 110 may not immediately notice the alarm, or the alarm may be suppressed before it emits an audible signal. Accordingly, alternative embodiments to FIGS. 5-8 include a step that determines whether a caregiver 110 is present in the room 130 when the alarm sounds; if a caregiver 110 is present, the alarm is not automatically suppressed by the presence of the caregiver 110. Computer 12 is configured to allow the alarm to sound for a predetermined amount of time so that the caregiver 110 can assess which alarm is sounding. Alternatively, computer 12 is configured to require the caregiver 110 to manually shut off the alarm. Conversely, if a caregiver 110 is not in the room 130, then the processes are the same as depicted in FIGS. 5-8.

Depending on the alarm priority, locking out patient controls may not be desirable. For example, if patient 100 experiences an incontinence event, the patient may desire to exit the bed to personally tend to his hygiene needs. However, locking out the bed controls can impede patient 100 from exiting the bed. Conversely, if the patient is experiencing a seizure, locking out the bed 90 controls and environmental devices 50 is desirable so to prevent a patient's involuntary movement from accidentally activating a bed 90 or environmental devices 50.

Figure 9:
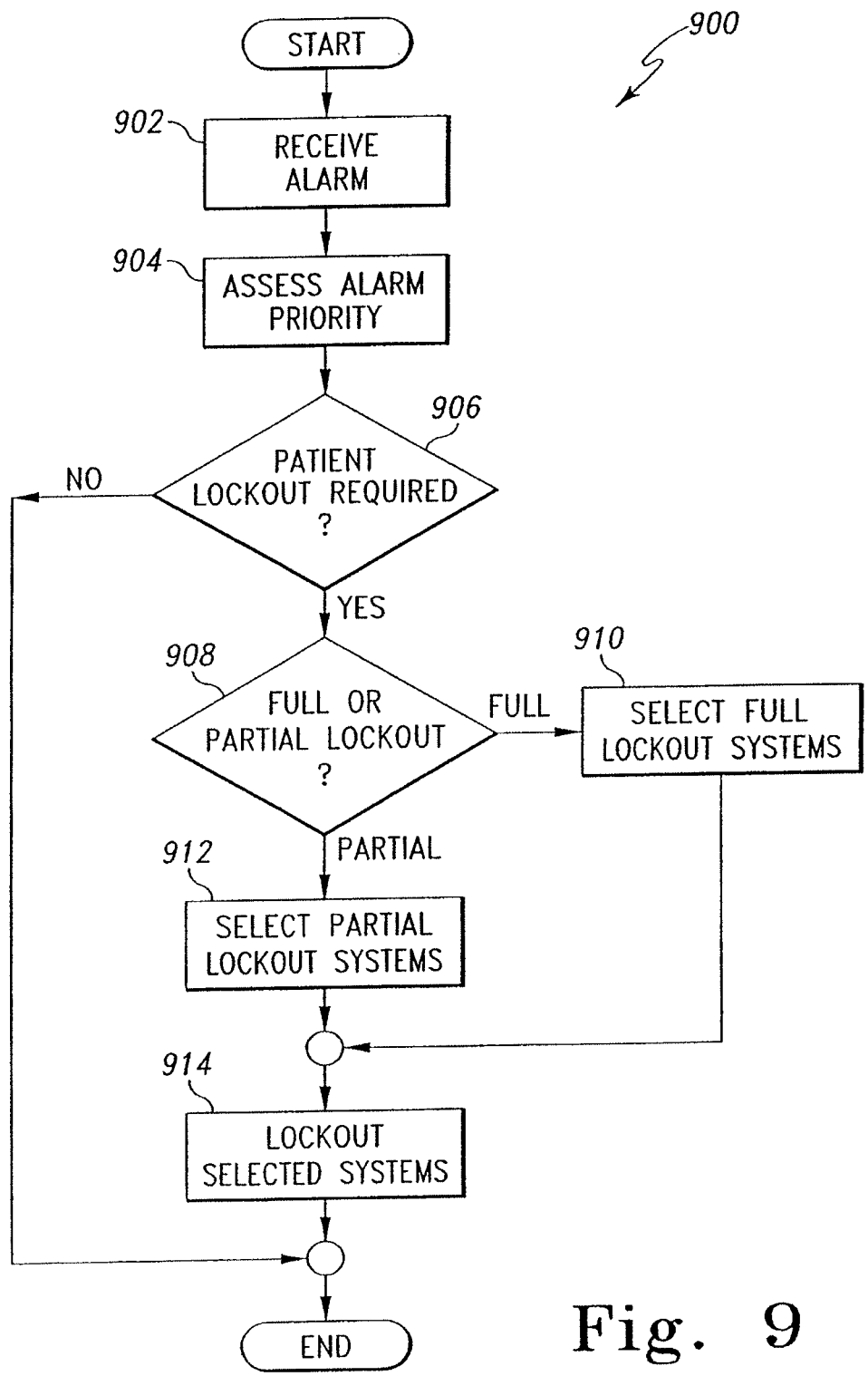
FIG. 9 is a flow chart of another illustrative embodiment describing a process that locks out patient bed controls and environmental controls based on the alarm priority.

FIG. 9 shows a flow chart 900 of another illustrative embodiment describing a process that locks out patient bed controls and environmental controls based on the alarm priority. In step 902, computer 12 receives an alarm. In step 904, the alarm priority is assessed. Step 906 determines whether a patient lock out is required. A higher priority alarm, such as a code blue or cardiac arrest alarm, will warrant locking out most, if not all, controls accessible by patient 90. Conversely, a lower priority alarm, such as an incontinence event, will warrant few, if any, control lock outs. Thus, step 908 determines whether a full lockout or a partial lockout is required. If a full lockout is required, step 910 selects all patient controls for lockout. Conversely, if only a partial lockout is required, step 912 selects which patient controls are to be locked out. The lockouts can either be preset in the system or manually set by hospital personnel. All selected controls are then locked out in step 914.

Similarly, depending on the priority of the alarm, the patient 100 environment may be prepared for the arrival of the caregiver 110. For example, if patient 100 experiences a cardiac arrest while watching television/radio 120, television/radio 120 will be immediately shut off. As a cardiac arrest usually warrants a response team, shutting off the television/radio 120 will ensure that this device will not distract any member of the response team. Conversely, if a patient 100 experiences only a slight incontinence event while watching television, which may not even be noticeable to the patient 100, the better therapy may be to let the patient 100 rest and tend to the patient 100 at a later time. As such, the television/radio 120 will not be shut off automatically. Thus, the environmental devices 50 may not be altered, based on the event magnitude of an associated alarm.

Figure 10:
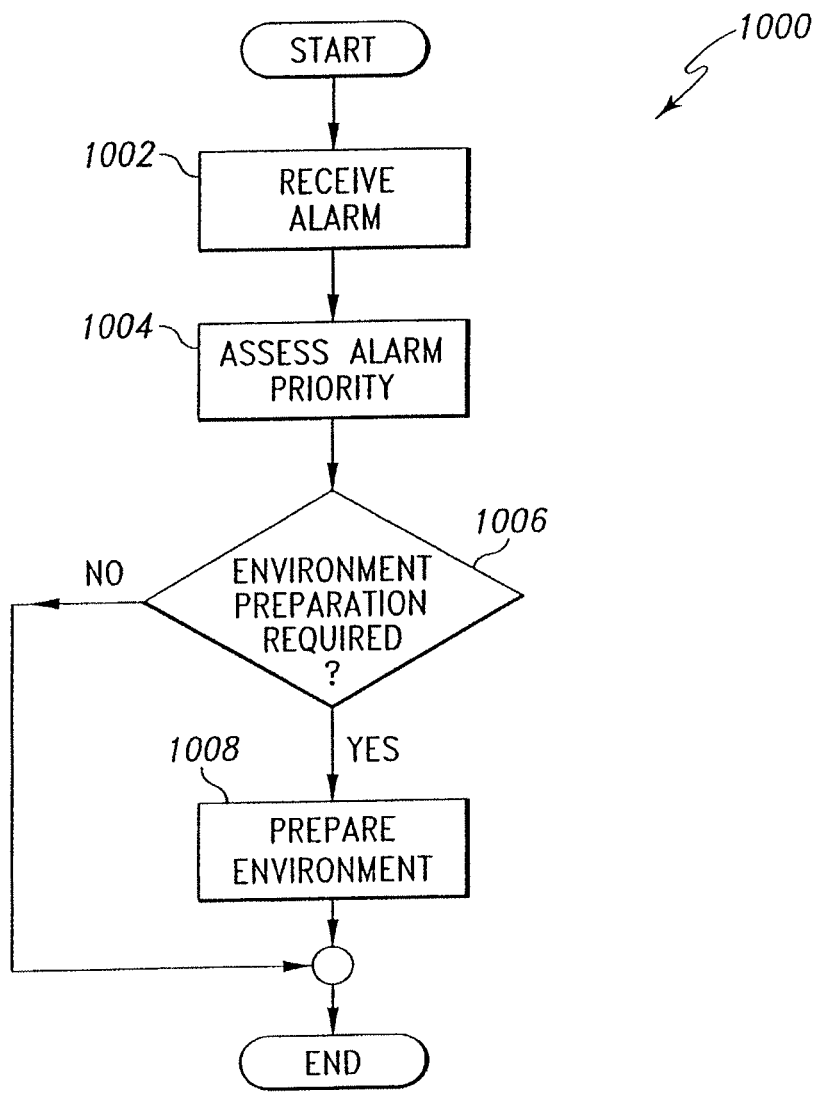
FIG. 10 is a flow chart of another illustrative embodiment describing a process that prepares the patient environment for the caregiver based on the alarm priority.

FIG. 10 shows a flow chart 1000 of another illustrative embodiment describing that process that prepares the patient environment for the caregiver based on the alarm priority. In step 1002, computer 12 receives an alarm. In step 1004, the alarm priority is assessed. Step 1006 determines whether environmental preparation is required. A higher priority alarm, such as a code blue or cardiac arrest alarm, will warrant environmental preparation. Conversely, a lower priority alarm, such as a slight incontinence event, will not require an environmental preparation. If an environmental preparation is required, the environment is prepared in step 1008.

Figure 11:
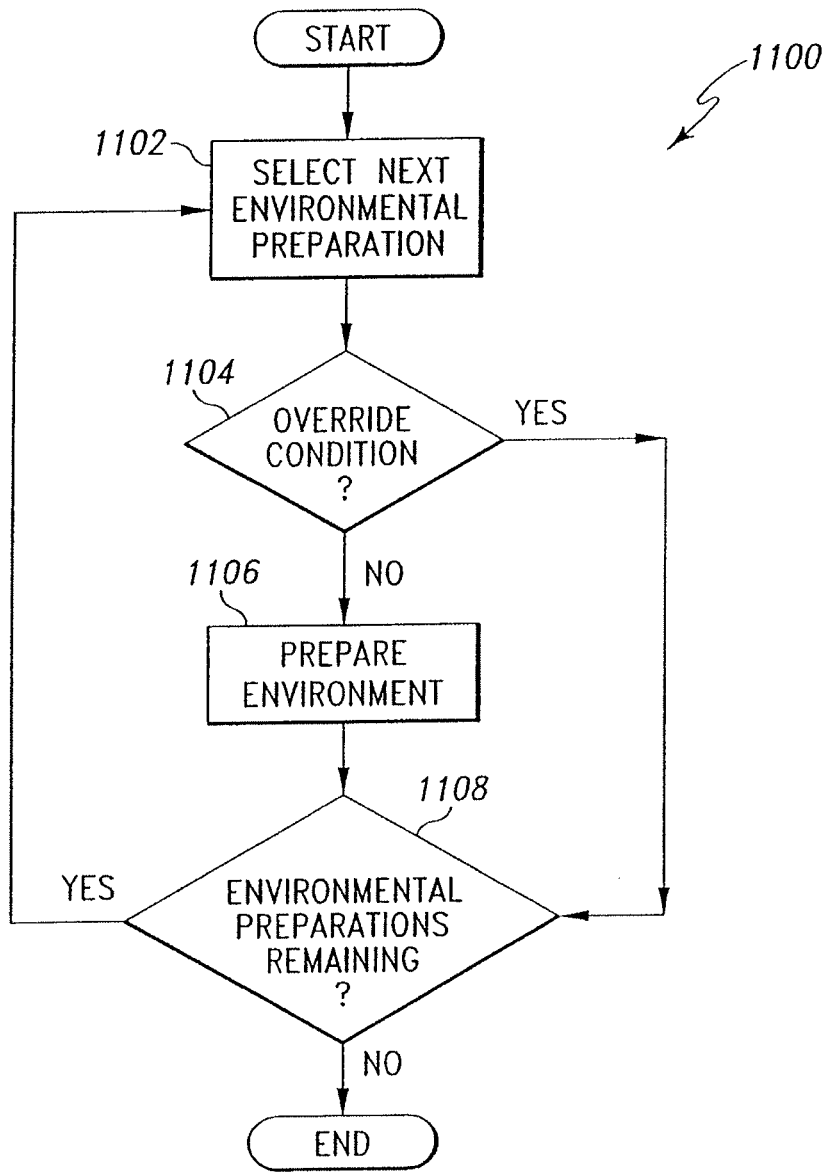
FIG. 11 is a flow chart of another illustrative embodiment describing a process that prepares the patient environment for the caregiver based on the alarm priority, with each environmental preparation subject to an override condition.

FIG. 11 shows a flow chart 1100 of another illustrative embodiment describing a process that prepares the patient environment for the caregiver based on the alarm priority, with each environmental preparation subject to an override condition. Illustratively, an environmental preparation can be subject to an override condition depending on the time of day. For example, if patient 100 experiences a cardiac arrest in the evening while sleeping, it is likely that room 130 lighting is low or off. Given the seventy of a cardiac arrest, which warrants a response team, an environmental preparation includes turning on the room 130 lighting. As such, overhead light 122 will immediately illuminate the room, as a response team will most likely arrive soon after the alarm is generated. Conversely, if a patient 100 experiences only a slight incontinence event during the evening while sleeping, the better therapy may be to let the patient 100 rest and tend to the patient 100 in the morning. As such, no environmental preparations is required and overhead light 122 remains off.

Once the environmental preparations are determined, step 1102 selects the next environmental preparation from the list, beginning with the first. In step 1104, the environmental preparation is checked for an override condition. Illustratively, overhead light 122, which normally would illuminate once an incontinence event is detected, will not illuminate if the time is outside visiting hours, e.g., from 8:00 PM-8:00 AM. If no override condition exists, the environment is prepared accordingly in step 1106; if an override condition for that particular environmental preparation exists, then the environment is not prepared with respect to that particular environmental preparation. If any environmental preparations remain, step 1108 repeats the process for the next environmental preparation. If no environmental preparations remain, then the process is complete.

Figure 12:
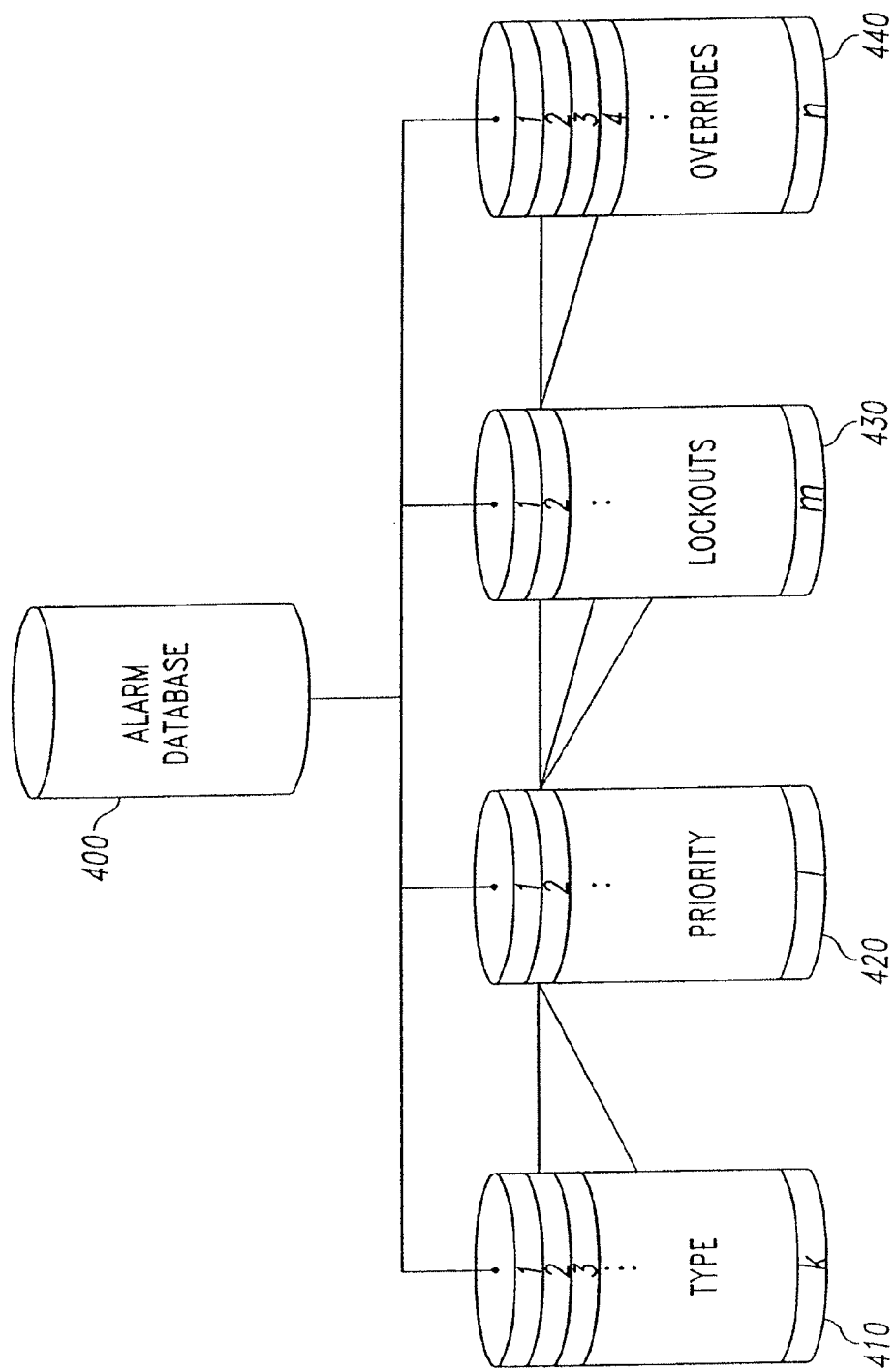
FIG. 12 depicts the database association of the alarm database, the database containing Type, Priority, Lockouts and Overrides fields.

The lockouts and overrides corresponding to an alarm can be configured through a common database structure. FIG. 12 depicts the database association of the alarm database 400, the database containing type 410, priority 420, lockout 430 and override 440 fields. The type 410 field stores the alarm type. Type 410 field contains records 1 ... k, priority 420 field contains records 1 ... 1, lockout 430 field contains records 1 ... m, and override 440 field contains record 1 ... n.

Illustratively, alarm types correspond to the equipment and/or patient 100 condition. Thus, type 410 values include "Incontinence Event", "Cardiac Arrest", "Low Blood Pressure", "Smoke Alarm", etc.

The priority 420 fields stores the alarm priority and corresponds the alarm priority to the alarm type. Illustratively, a higher alarm priority corresponds to more immediate needs of the patient 100 or possibly a life threatening condition the patient 100 is experiencing. As shown in FIG. 12, two records from the type 410 field have been assigned a priority 2. Thus, if an alarm corresponding to either of those two records is received, it is assigned priority 2.

The lockouts 430 field stores the patient lockouts, the environmental lockouts, and environmental preparations. Illustratively, the lockouts correspond to the alarm priority. As shown in FIG. 12, a priority 2 alarm has been assigned three lockouts. Illustratively, the lockouts correspond to bed 90 siderails, overhead light 122, and television/radio 120. Thus, if a priority 2 alarm is received, the patient will not be able to operate the bed 90 siderails, overhead light 122, and television/radio 120.

The override 440 field stores overrides corresponding to the lockouts 430. As shown in FIG. 12, one lockout has two potential overrides. Illustratively, the lockout corresponds to the bed 90 siderail, and the override conditions are "Visiting Hours" or "Minor Incontinence Event." Thus, if a patient 90 experiences an incontinence event that is only a minor event, the bed 90 siderails will not be locked out. Additionally, if the incontinence event occurs during visiting hours, the bed 90 siderails will not be locked out.

One of ordinary skill in the art will readily appreciate that the database configuration of FIGS. 3, 4 and 12 are illustrative only, and that other configurations or structures are readily apparent. For example, overrides can be correlated to priority, or priority and lockouts, etc. Furthermore, the illustrative fields are not exhaustive and other categorization schemes exist known to those of ordinary skill in the art.

Although the invention has been described in detail with reference to certain illustrated embodiments, variations exist within the scope and spirit of the invention as described and as defined in the following claims.

What is claimed is:

1. A system comprising
   a patient bed having controls that are used by a patient to control functions of the patient bed, and
   a monitoring system configured to detect a presence of a caregiver in a vicinity of the patient bed, wherein at least some of the controls are locked out from use by the patient in response to the monitoring system detecting the presence of the caregiver.

2. The system of claim 1, wherein the patient bed has an alarm and wherein, if the alarm is sounding when the caregiver is not detected by monitoring system, the alarm becomes silenced in response to the monitoring system detecting the presence of the caregiver.

3. The system of claim 1, wherein the patient bed has an alarm and wherein the alarm is required to be silenced by the caregiver if the alarm sounds while the caregiver is detected by the monitoring system.

4. The system of claim 1, wherein the patient bed has an alarm and wherein the alarm is automatically silenced after a predetermined amount of time if the alarm is sounded when the caregiver is detected by the monitoring system.

5. The system of claim 1, wherein the patient bed has an alarm and wherein at least one of the controls is locked out in response to activation of the alarm.

6. The system of claim 1, further comprising a computer that is communicatively coupled to the patient bed and to an associated device that is located in the vicinity of the patient bed.

7. The system of claim 6, wherein the associated device has an alarm and wherein the computer is configured to detect the alarm being active and signal the patient bed to lock out at least one of the controls in response to the alarm being active and the presence of the caregiver not being detected by the monitoring system.

8. The system of claim 6, wherein the associated device has an alarm, wherein the computer includes a caregiver database associating the caregiver with the patient, and the computer is configured to silence the alarm when the caregiver associated with the patient is detected by the monitoring system.

9. The system of claim 6, wherein the associated device has an alarm and wherein the computer is configured to detect the alarm and alter the patient bed when the alarm is detected.

10. The system of claim 9, wherein the computer is configured to determine an override for the patient bed and not alter the patient bed if the override exists.

11. The system of claim 10, wherein the override is based on a time of day.

12. The system of claim 10, wherein the override is based on an event magnitude of the alarm of the associated device.

13. The system of claim 1, wherein the patient bed further comprises a plurality of lockouts each of which is configured to prevent actuation of an associated one of the controls based on a lockout status and wherein changes to the lockout status are prevented when the presence of the caregiver is not detected by the monitoring system.

14. The system of claim 1, wherein the monitoring system comprises a locating and tracking system and further comprising a computer coupled to the locating and tracking system and coupled to the patient bed.

15. The system of claim 1, further comprising a computer communicatively coupled to the patient bed and to the monitoring system and further comprising a plurality of associated devices communicatively coupled to the computer.

16. The system of claim 15, wherein the plurality of associated devices comprise two or more of the following: a patient monitor, a treatment device, a therapy device, and an environmental device.

17. The system of claim 15, wherein each of the plurality of associated devices has an alarm and wherein, if any of the alarms of the plurality of associated devices are being sounded, the alarm is silenced in response to the monitoring system detecting the presence of the caregiver.

18. The system of claim 15, wherein each of the associated devices has an alarm and wherein the computer signals the patient bed to lock out at least one of the controls in response to the alarm being activated.

* * * * *